United States Patent [19]

Nikravech et al.

[11] Patent Number: 5,053,575

[45] Date of Patent: Oct. 1, 1991

[54] METHOD OF CONVERSION OF NATURAL GAS OR OF LIGHT ALKANES INTO UNSATURATED HYDROCARBONS

[75] Inventors: Mehrdad Nikravech; Isabelle Vedrenne, both of Paris; Jacques Amouroux, Bures sur Yvétte; Jacques Saint-Just, Le Pecq, all of France

[73] Assignee: Gaz de France, Paris, France

[21] Appl. No.: 440,301

[22] Filed: Nov. 22, 1989

[30] Foreign Application Priority Data

Nov. 24, 1988 [FR] France ............................... 88 15362

[51] Int. Cl.$^5$ .......................................... C01C 15/393
[52] U.S. Cl. ................................ 585/500; 585/943; 585/415; 585/541
[58] Field of Search ............................... 585/943, 500

[56] References Cited

U.S. PATENT DOCUMENTS

| | | | |
|---|---|---|---|
| 1,880,189 | 9/1932 | Snelling | 585/500 |
| 3,192,280 | 6/1965 | Landgren | 585/500 |
| 4,487,683 | 12/1984 | Bozzuto | 585/943 |
| 4,599,474 | 7/1986 | Devries et al. | 585/500 |
| 4,608,444 | 8/1986 | Baerno et al. | 585/500 |
| 4,704,487 | 11/1987 | Devries et al. | 585/500 |
| 4,704,493 | 11/1987 | Devries et al. | 585/500 |
| 4,761,515 | 8/1988 | Gondouin | 585/943 |
| 4,814,533 | 5/1984 | Devries et al. | 585/943 |

*Primary Examiner*—Helane E. Myers
*Attorney, Agent, or Firm*—Kenyon & Kenyon

[57] ABSTRACT

A method of converting natural gas or light alkane(s) into unsaturated hydrocarbons, consisting in providing inside of a reaction space a fluidized bed of particles of a refractory and advantageously catalytic material and feeding a plasma of a hydrogen-containing gas and the natural gas or the light alkane(s) into the bed so that the latter effects the quenching of the reaction medium and catalyses the conversion reaction.

16 Claims, 1 Drawing Sheet

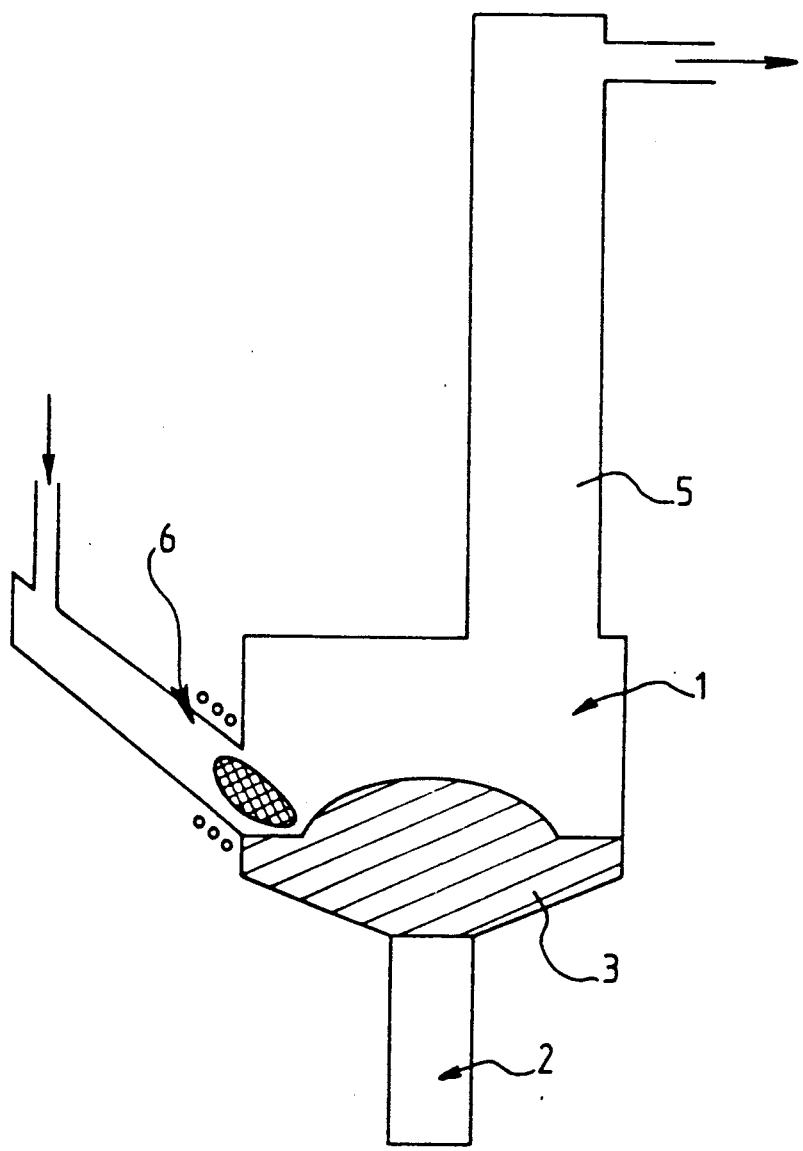

METHOD OF CONVERSION OF NATURAL GAS OR OF LIGHT ALKANES INTO UNSATURATED HYDROCARBONS

FIELD OF THE INVENTION

The present invention relates to a method of conversion of natural gas or of light alkane(s) into unsaturated hydrocarbons and more particularly to a method of conversion with supply of electric energy applied in particular in the chemical and power generating industries.

BACKGROUND OF THE INVENTION

Presently there are methods of conversion with supply of electric energy. A representative method is the Hüls process which makes possible the conversion of hydrocarbons such as methane into unsaturated hydrocarbons and in particular into acetylene. This process consists in passing methane into an electric arc and then in separating the products obtained. This process however has the inconvenience of generating a very substantial amount of carbon black.

Therefore an improvement has been proposed by using a hydrogen plasma. The hydrogen plasma allows to supply the energy required by the methane conversion reaction which is an endothermal reaction. This energy is supplied in situ by the plasma-producing gases without the agency of a wall. While plasma however is a source of power in the methane conversion reaction it still exhibits inconveniences since its temperature is too high for the reaction contemplated. Indeed methane brought to a temperature above 1,200° C. would break down through a sequence of reactions of dehydrogenations and cyclizations into a mixture of polyaromatic substances leading to carbon black.

These methods therefore are not fully satisfactory since they involve an excessive build up of carbon black of uncontrolled quality which therefore becomes a by-product difficult to valorize.

SUMMARY OF THE INVENTION

The object of the invention is a method which does not exhibit the difficulties and the inconveniences of the known methods.

To reach that aim the invention is characterized by the steps of providing inside of a reaction space a fluidized bed of particles of a refractory and advantageously catalytic material and in feeding a plasma of a gas containing hydrogen and natural gas or light alkane(s) into the bed so that the latter performs a quenching of the reaction medium and catalyses the conversion reaction.

According to a characterizing feature of the invention the bed of particles is fluidized by a fluidizing gaseous stream advantageously containing hydrogen.

According to still another characterizing feature of the invention the gaseous fluidizing stream contains hydrogen and argon.

According to a preferred embodiment of the invention the natural gas or the light alkane(s) is fed into the bed together with the fluidizing gaseous stream and the light alkane is methane. The fluidizing hydrogen and methane are fed into the bed in a hydrogen/methane proportion ranging from 0.5 to 10 and preferably from 2 to 5.

According to a further characterizing feature of the invention the fluidizing gaseous stream is pre-heated upstream of the bed to a temperature lying between 50° C. and 500° C. and preferably between 150° C. and 350° C.

According to a particular feature of the method of the invention a plasma containing at least 10% of hydrogen and which may contain argon is fed into the bed.

According to another particular feature of the invention the bed consists of particles of a material selected in particular from the group consisting of oxides, carbides, nitrides and borides.

According to another particular feature of the invention the particles produce a catalytic effect.

According to still a further particular feature of the invention the bed contains more than one catalyst.

The conversion reaction is carried out within the bed at a temperature lying between 500° C. and 1,200° C. and preferably between 500° C. and 800° C.

BRIEF DESCRIPTION OF THE DRAWING

The invention will be better understood and further objects, characterizing features, details and advantages thereof will appear more clearly as the following explanatory description proceeds with reference to the accompanying diagrammatic drawing given by way of non limiting example only and the single FIGURE of which shows a sketch of a preferred embodiment of the invention.

DESCRIPTION OF THE PREFERRED EMBODIMENT

The method according to the invention is put into practice by means of a device of the kind shown in the accompanying drawing and comprising an enclosure 1 comprising at the level of its bottom means 2 for injecting a fluidizing gaseous stream, outlet means (not shown) for the latter, containing a body of particles of a material adapted to build up a fluidized bed 3 and a plasma torch 6 operating with a plasma of a gas containing hydrogen and adapted to feed the plasma inside of the enclosure into the bed of fluidized particles.

There is provided a discharge pipe 5 connected to the outlet of the enclosure.

The plasma torch is connected to a wall of the enclosure shell so that the plasma be fed into the fluidized bed. It is possible to vary the angle of insertion of the torch into the enclosure shell from 0° to 90°. Preferably the angle of insertion of the torch is 20° with respect to the horizontal section of the enclosure. Typically this torch consists of two concentric silica tubes with an outer diameter of 30 mm, surrounded by five hollow inductive copper turns cooled by water and through which a high-frequency electric current is flowing.

The inner wall of the shell 1 is made for instance from 4 mm thick refractory alumina thermally insulated by a 20 mm thick layer of porous bricks. The whole is covered with glass wool and with an asbestos strip or tape. The size of the shell is larger than that of the plasma thereby avoiding the direct contact of the walls with the hot area of the plasma. The shell comprises a pyramidal zone in which the particles are caused to be suspended and thermocouples (not shown) are arranged within the shell to measure the temperature of the fluidized bed. A hemispheric lap (not shown) arranged on one of the sides of the shell allows the introduction of the treating plasma as well as of the whole of the particles.

The means 2 for injecting the fluidizing gaseous stream comprise for instance a 40 mm opaque silica tube surrounded by a heating tape and filled with refractory balls; this system allows the gases to be preheated and a thermocouple (not shown) is provided within the tube to control the temperature of the fluidizing gases.

The discharge tube or pipe 5 consists for instance of a quartz tube with a diameter of 85 mm and a length of 500 mm and thermocouples (not shown) are arranged within this tube for measuring the temperature of the gaseous stream flowing therethrough. The outlet of this tube may be connected to a water heat exchanger (not shown) wherein the reaction mixture is cooled before being taken off for analysis purposes.

The bed consists of particles of a material selected in particular from the group consisting of oxides, carbides, nitrides and borides. The following list may be set up by way of illustrative examples:

| oxides | of aluminum | $Al_2O_3$ |
| --- | --- | --- |
|  | of magnesium | $MgO$ |
|  | of calcium | $CaO$ |
|  | of beryllium | $BeO$ |
|  | of cerium | $CeO$ |
|  | of thorium | $ThO_2$ |
|  | of hafnium | $HfO_2$ |
|  | of lanthanum | $La_2O_3$ |
|  | and other mixed oxides |  |
| carbides | of silicon | $SiC$ |
|  | of thorium | $ThC$ |
|  | of boron | $B_4C$ |
| nitrides | of boron | $BN$ |
|  | of hafnium | $HfN$ |
|  | of zirconium | $ZrN$ |
| borides | of thorium | $ThB_4$ |
|  | of niobium | $NbB_2$ |
|  | of zirconium | $ZrB_2$ |
| carbon | (graphite) | $C$ |

Whatever the nature of the materials used might be they have to be refractory because the particles of the bed should be capable of withstanding high temperatures since they are in contact with the plasma jet. The bed particles may themselves play the function of a catalyst and it is also possible to add another catalyst thereto.

It should be understood that the word "catalyst" is taken in its broad meaning, i.e. the particles may accelerate certain desired reactions or inhibit certain undesired reactions as the build up of carbon black or coke.

With the method according to the present invention the bed particles are fluidized into a springing bed by the supply flow of a fluidizing gaseous stream consisting mainly of hydrogen and of a mixture of hydrogen and argon fed into the shell 1 with the assistance of injection means 2 and the natural gas or the light alkane(s) to be converted are caused to be fed into the bed thus fluidized. Preferably as illustrated in the device shown on the FIGURE natural gas or light alkane(s) is fed into the fluidized bed together with a fluidizing gaseous stream. The optimum amount of fluidizing hydrogen is determined so as to minimize the production of carbon black. The fluidizing gases are preheated upstream of the bed within the tube 2 to a temperature lying between 50° C. and 500° C. and preferably between 150° C. and 350° C.

The plasma torch 6 is injecting a hydrogen plasma which may contain argon and containing at least 10% of hydrogen into the fluidized bed of particles where a homogeneous transfer of heat is effected between the plasma and the fluidized bed thereby allowing a conversion reaction to be carried out in the presence of free hydrogen radicals at an adjusted temperature which remains substantially below that of the plasma whereby the building up of carbon black is therefore minimized.

The unsaturated hydrocarbons obtained by the conversion reaction achieved inside of the fluidized bed are then discharged through the tube 5. The thermocouples arranged within this tube allow the temperatures to be measured.

The use of a fluidized bed in the method according to the invention offers substantial advantages for the following reasons:

its heat transfer properties make possible an effective quenching of the plasma;

its viscosity substantially equal to that of the plasma provides for a very good mixture between the latter and the fluidized bed; and its possible catalytic properties may provide for the direct transformation of the product(s) to be converted into unsaturated hydrocarbons.

Furthermore the nature of the material of the particles forming the bed and/or the nature of the catalyst make it possible to direct the conversion towards the desired products.

The eight following examples are given with the purpose of well showing the advantages of the present invention.

As a general rule the examples have been carried out as follows:

The plasma torch operates at a frequency of 5 MHz with a power of 4.4 kW. The injection angle is 20°. The plasma-generating gases fed in are argon with a flow rate of 30 l/mn and hydrogen with a flow rate of 5 l/mn. The bed consists of alumina particles (650 g) with a mean diameter of 300 microns. The bed particles are fluidized by a mixture of methane, hydrogen and argon. Through a setting of the flow rates of these three gases the time during which methane is left in the reactor is adjusted. A good fluidization is obtained with a total flow rate lying between 15 l/mn and 40 l/mn. The optimum of fluidizing hydrogen is determined with respect to that of methane in order to minimize the build up of carbon black. This ratio is lying between 0.5 and 10 and preferably between 2 and 5. The fluidizing gases are preheated to a temperature lying between 50° C. and 500° C., preferably between 150° C. and 350° C. The flow rates of the plasma-producing and fluidizing gases are measured and adjusted by means of mass flowmeters. Thermocouples are installed to allow the measuring of the temperature of the fluidizing gases upstream of the shell, of the shell wall, of the fluidized bed and the temperatures within the pipe 5.

The temperature of the fluidized bed is selected as a reference temperature since on the one hand it would characterize the effectiveness of the quenching and on the other hand because the conversion reaction takes place within the fluidized bed.

The analysis of the products is made through gas chromatography.

EXAMPLES

The eight examples are detailed in the following tables 1 and 2. They have been effected with the same mass of identical particles and under identical operating conditions of the torch. They differ from each other by the flow rates of the fluidizing gases and by the average temperature of the fluidized bed. The results obtained with these various examples are also given in detail in the following tables 1 and 2.

TABLE 1

OPERATING CONDITIONS AND ANALYSIS RESULTS

| Ex. N° | Mean Temperature in the fluidized bed, °C | Fluidizing gas (l/mn) | | | Molar composition of the conversion products (%) | | | |
|---|---|---|---|---|---|---|---|---|
| | | Ar | $H_2$ | $CH_4$ | $(C_2H_2)$ | $(C_2H_4)$ | $(C_2H_6)$ | (C) |
| 1 | 580 | 11 | 8 | 5 | 11 | 2.5 | 0.5 | 11.5 |
| 2 | 700 | 11 | 8 | 5 | 9 | 2 | 0.4 | 17 |
| 3 | 770 | 11 | 8 | 5 | 6 | 2 | 0.4 | 30 |
| 4 | 500 | 15 | 8 | 5 | 1.5 | 0.3 | 0.1 | 5 |
| 5 | 600 | 6 | 8 | 5 | 4 | 1.5 | 0.3 | 22 |
| 6 | 600 | 0 | 8 | 5 | 7 | 2.5 | | 28 |
| 7 | 550 | 0 | 13 | 5 | 21 | 13.5 | 2 | 5 |
| 8* | 580 | 11 | 8 | 5 | 0.2 | 0 | 0 | 0.3 |

*torch stopped
(C) = carbon black concentration

TABLE 2

RESULTS

| Example N° | $CH_4\%$ Conversion | $C_2\%$ Selectivity | $C_2\%$ Efficiency |
|---|---|---|---|
| 1 | 34 | 71 | 24 |
| 2 | 35 | 57 | 20 |
| 3 | 43 | 40 | 17 |
| 4 | 9 | 42 | 3.8 |
| 5 | 32 | 34 | 11 |
| 6 | 43 | 38 | 16 |
| 7 | 57 | 94 | 53 |
| 8* | 0.7 | 57 | 4 |

*torch stopped

The results obtained and listed in tables 1 and 2 show all the interest of the method and in particular prove the effectiveness of the quenching by the fluidized bed since the average temperature therein is relatively low (lying between 500° C. and 800° C.).

The examples 1 to 3 have been carried out under identical fluidizing conditions but at three different temperatures. The results show that the amount of carbon black built up increases very quickly with temperature. It appears from these results that the temperature control is of prime importance and all the interest in quenching the plasma may thus be appreciated.

Example 4 has been carried out at a temperature of 500° C. It should be pointed out that the conversion rate of $CH_4$ at this temperature is 9% only. Therefore a temperature of about 500° C. would be the lower limit for the conversion of methane.

The examples 5 and 6 have been performed at a same temperature but with a different fluidizing flow rate. An increase in the conversion rate is ascertained when the fluidizing gas flow rate decreases, i.e. when the residence time of methane increases. The control of this important parameter may thus be performed easily.

If examples 6 and 7 are compared to each other a sharp increase in $C_2$ efficiency may be noted, certainly due to the increase in their hydrogen/methane ratio. The part played by fluidizing hydrogen is multiple. In particular it would inhibit the dehydrogenation reactions leading to carbon black and it would "protect" methane against thermal shocks but it may also limit the conversion reaction hence the necessity of determining its optimum concentration.

Example 8 has been carried out in order to observe the specific part played by the plasma which is to supply free radicals generating species in large concentrations. For this purpose a simple experience has been run which consists in stopping the torch and in forthwith analysing the reaction mixture. It should be pointed out that at a same temperature but without plasma the methane conversion rate is negligible.

Although these examples have been obtained without optimizing the operating parameters the very good results of example 7 may be noted, wherein the $C_2$ (acetylene) selectivity is 94%, i.e. already better than that of the Hüls process which is of about 74%.

The methane conversion as defined by the ratio of the amount of converted methane to the total amount of methane fed in. It is computed as follows:

$$C = \frac{2(C_2H_2) + 2(C_2H_4) + 2(C_2H_6) + (C)}{2(C_2H_2) + 2(C_2H_4) + 2(C_2H_6) + (C) + (CH_4)}$$

with (X) meaning the molar concentration of the component X in the reaction mixture given by the chromatographic analysis.

The $C_2$ selectivity is the ratio of the amount of $C_2$ products obtained to the amount of conversion products. It is calculated as follows:

$$S = \frac{2(C_2H_2) + 2(C_2H_4) + 2(C_2H_6)}{2(C_2H_2) + 2(C_2H_4) + 2(C_2H_6) + (C)}$$

The $C_2$ efficiency is defined by the ratio of the amount of $C_2$ products obtained to the amount of methane fed in. It is computed as follows:

$$R = \frac{2(C_2H_2) + 2(C_2H_4) + 2(C_2H_6)}{2(C_2H_2) + 2(C_2H_4) + 2(C_2H_6) + (C) + (CH_4)}$$

It should be understood that the invention is not at all restricted to the embodiments described and shown which have been given by way of illustrative examples only. Thus according to the nature of the catalyst and of the batch and to the operating conditions, it is possible to obtain hydrocarbons higher than $C_2$. Moreover it would be possible to feed the products to be converted into the fluidized bed differently from the example shown, i.e. separately from fluidizing gas at any suitable place on condition of allowing the plasma to be quenched by the fluidized bed. It should also be understood that the plasma used may be produced in any manner whatsoever, in particular by means of a blown or transferred electric arc or also through induction.

What is claimed is:

1. A method of conversion of natural gas or light alkane(s) into unsaturated hydrocarbons wherein a natural gas or light alkane(s) is contacted with a plasma of a hydrogen-containing gas within a reaction space including a bed of catalytic material and said unsaturated hydrocarbons are recovered at the outlet of said reaction space, said method comprising the steps of:
   a) using as a catalytic material, a material formed of refractory fluidizable particles;
   b) causing said catalytic, refractory particles to form a fluidized bed of particles inside said space;
   c) feeding said plasma into said fluidized bed at a first zone of said bed; and
   d) feeding said natural gas or light alkane(s) at a second zone of said bed distant from said first zone, to produce a homogeneous transfer of heat between said plasma and said fluidized bed before the plasma comes into contact with said natural gas of light alkane(s), and thus causing said conversion reaction to be carried out at a temperature below the temperature of said plasma before said plasma enters into said bed.

2. A method according to claim 1, wherein said bed of particles is fluidized by a fluidizing gaseous stream containing hydrogen.

3. A method according to claim 2, wherein said fluidizing gaseous stream contains hydrogen and argon.

4. A method according to claim 2, wherein said natural gas or said light alkane(s) is fed into the bed together with the fluidizing gaseous stream.

5. A method according to claim 1, wherein the light alkane is methane.

6. A method according to claim 2, wherein the hydrogen and methane are fed in with a hydrogen/methane proportion ranging from 0.5 to 10.

7. A method according to claim 2, wherein the fluidizing gaseous stream is preheated to a temperature lying between 50° C. and 500° C.

8. A method according to claim 6, wherein the hydrogen/methane proportion ranges from 2 to 5.

9. A method according to claim 7, wherein the preheating temperature of the fluidizing gaseous stream is between 150° C. and 350° C.

10. A method according to claim 1, further consisting in supplying a plasma containing at least 10% of hydrogen.

11. A method according to claim 8, consisting in supplying a plasma containing hydrogen and argon.

12. A method according to claim 1, wherein the bed consists of particles of a material selected in particular from the group consisting of oxides, carbides, nitrides and borides.

13. A method according to claim 8, wherein the particles have a catalytic effect.

14. A method according to claim 8, wherein the bed contains more than one catalyst.

15. A method according to claim 1, wherein the conversion reaction is carried out at a temperature lying between 500° C. and 1,200° C.

16. A method according to claim 15, wherein the temperature of the conversion reaction is between 500° C. and 800° C.

* * * * *

UNITED STATES PATENT AND TRADEMARK OFFICE
CERTIFICATE OF CORRECTION

PATENT NO. : 5,053,575
DATED : October 1, 1991
INVENTOR(S) : Mehrdad NIKRAVECH et al.

It is certified that error appears in the above-indentified patent and that said Letters Patent is hereby corrected as shown below:

| Column | Line | |
|--------|------|---|
| 1 | 26 | Change "to supply" to --the supply of--. |
| 3 | 62 | Change "is injecting" to --injects--. |
| 4 | 42 | Change "is lying" to --lies--. |
| 5 | 32 | Change "all the interest" to --the effectiveness--. |
| 5 | 41 | Change "all the interest" to --the effectiveness--. |
| 5 | 66 | Change "experience" to --experiment--. |
| 8 | 7 | Change "claim 8" to --claim 10--. |
| 8 | 13 | Change "claim 8" to --claim 12--. |
| 8 | 15 | Change "claim 8" to --claim 12--. |

Signed and Sealed this

Twelfth Day of July, 1994

Attest:

BRUCE LEHMAN

Attesting Officer    Commissioner of Patents and Trademarks